United States Patent [19]

Hess et al.

[11] 4,169,895

[45] Oct. 2, 1979

[54] ANTISECRETORY 16,16-DIMETHYL-17-OXAPROSTAGLAN-DINS

[75] Inventors: Hans-Jürgen E. Hess, Old Lyme; Michael R. Johnson, Gales Ferry, both of Conn.

[73] Assignee: Pfizer Inc., New York, N.Y.

[21] Appl. No.: 830,159

[22] Filed: Sep. 2, 1977

Related U.S. Application Data

[63] Continuation-in-part of Ser. No. 727,463, Sep. 28, 1976, abandoned.

[51] Int. Cl.$^2$ ............... C07C 103/19; C07C 143/75; A61K 31/16; A61K 31/18
[52] U.S. Cl. ........................ 424/320; 260/556 A; 260/556 AC; 260/557 R; 260/558 R; 260/561 R; 424/321; 424/324
[58] Field of Search ........... 260/556 A, 557 R, 558 R, 260/561 R, 556 AC; 424/320, 321, 324

[56] References Cited

U.S. PATENT DOCUMENTS

| | | | |
|---|---|---|---|
| 3,816,393 | 6/1974 | Hayashi et al. | 536/103 |
| 3,927,197 | 12/1975 | Monkhouse | 260/557 R X |
| 3,954,741 | 5/1976 | Schaaf et al. | 260/556 A X |
| 3,981,868 | 9/1976 | Bernady et al. | 260/557 R X |
| 4,060,534 | 11/1977 | Bundy | 260/408 |
| 4,061,671 | 12/1977 | Beck et al. | 560/121 X |
| 4,098,805 | 7/1978 | Bundy | 260/557 R X |
| 4,130,584 | 12/1978 | Bundy | 260/556 AR X |

FOREIGN PATENT DOCUMENTS 1345934 2/1974 United Kingdom .

OTHER PUBLICATIONS

Collins et al., ". . . . Prostaglandins," Tetrahedron Letters, No. 48, pp. 4217–4220, 1975.

*Primary Examiner*—Thomas Waltz
*Attorney, Agent, or Firm*—Connolly and Hutz

[57] ABSTRACT

N-alkylsulfonyl, N-alkanoyl and N-benzoyl 16,16-dimethyl-17-oxaprostaglandin $E_2$ and $E_1$ carboxamides having antisecretory biological activity as well as intermediates for their synthesis are disclosed.

10 Claims, No Drawings

ANTISECRETORY 16,16-DIMETHYL-17-OXAPROSTAGLANDINS

This is a continuation-in-part of application Ser. No. 727,463 filed Sept. 28, 1976, and now abandoned.

BACKGROUND OF THE INVENTION

The $C_{20}$ unsaturated fatty acids, known as prostaglandins, form a large family of naturally-occurring compounds. Their structure, biological activities and medicinal use have been variously described in U.S. Pat. Nos. 3,971,826, 3,984,400 and in application Ser. No. 727,463, now abandoned.

One of the principal goals guiding the preparation of synthetic pharmaceutical agents is the development of compounds which are highly selective in their pharmacological activity and which have an increased duration of activity over their naturally-occurring congeners. In a series of compounds similar to the naturally-occurring prostaglandins, increasing selectivity of a single compound usually involves enhancement of one prostaglandin-like physiological effect and the diminution of the others. The potential benefits of this selectivity are manifold; e.g., a decrease in the severe side effects such as diarrhea and emesis which are frequently observed following administration of the natural prostaglandins. A separation of cardiovascular and bronchodilator activity which are both embraced by natural prostaglandins also would have obvious medicinal potential. Recent developments directed toward an increase of biological selectivity include the 16,16-dimethyl prostaglandins [B. J. Magerkin, et al., *Prostaglandins*, 4, 143 (1973)], 17-oxaprostaglandin $F_2\alpha$ [J. Bowler, et al., *Prostaglandins*, 9, 391 (1975); 10, 5 (1975)], 16,16-dialkyl (including dimethyl)-17, 18 or 19-oxaprostaglandin $E_2$, $E_1$, $F_{2\alpha}$, $F_{1\alpha}$; the 11, 15-bis- THP ethers of those compounds; [Belgium 827,529]; 16,16-dimethyl-17-oxaprostaglandin $E_2$, $E_1$, $F_{2\alpha}$ $F_{1\alpha}$ and the 11,15-bis THP ethers of those compounds [Belgium 832,479] and N-substituted prostaglandin carboxamides including N-alkylsulfonyl, N-alkanoyl and N-benzoyl $PGE_2$ and $PGE_{2\alpha}$ carboxamides [U.S. 3,954,741].

SUMMARY OF THE INVENTION

The present invention comprises prostaglandin compounds which have selective and potent biological activity and includes the N-alkylsulfonyl, N-alkanoyl and N-benzoyl carboxamides of 16,16-dimethyl-17-oxaprostaglandin $E_2$ and 16,16-dimethyl-17-oxaprostaglandin $E_1$, having from one to four carbon atoms in the alkylsulfonyl group and two to five carbon atoms in the alkanoyl group and the 15β isomers of these compounds.

In addition, the present invention comprises the bis-11,15-THP ethers of the prostaglandin E compounds as well as the corresponding $F_{2\alpha}$ and $F_{1\alpha}$ compounds.

Of special interest as an agent which can be used for inhibition of gastric acid secretion is N-(Methanesulfonyl and acetyl)-9-oxo-11α, 15α-dihydroxy-16,16-dimethyl-17-oxa-cis-5-trans-13-prostadienamide described above as a member of the present invention.

DETAILED DESCRIPTION OF THE INVENTION

The 16,16-dimethyl-17-oxaprostaglandin compounds of the instant invention are prepared by a three-part sequence which is predicated upon the synthesis of the ω or bottom side chain, proceeds to the synthesis of the α or top side chain and ends with the conversion of the synthesized $PGF_{2\alpha}$ intermediate into the array of final products. The sequence, which is presented in Schemes A, B, C and D employs as a starting material the known compound 2-(3α-p-phenylbenzoyloxy-5α-hydroxy-2β-formyl cyclopent-1α-yl)acetic acid, γ-lactone of formula A [E. J. Corey, et. al., *J. Am. Chem. Soc.*, 93, 1491 (1971)].

With regard to the particular steps of the sequence, it is recognized that the chemical methods used herein are known to those familiar with the prostaglandin art. For instance, the reactions described herein as Wittig reactions, Jones oxidations, Wadsworth-Emmons reactions and Superhydride reductions are modeled after the methods of Corey and others (E. J. Corey, et. al., *J. Amer. Chem. Soc.*, 93, 1491 (1971); E. J. Corey, et. al., *J. Amer. Chem. Soc.* 92,2586 (1970); U.S. 3,883,513).

The synthetic sequence of Scheme A illustrates the formation of the ω-chain. The first step (a) unites the γ-lactone of formula A with Phosphonate B to complete the backbone of the ω-chain.

To prepare the novel phosphonate reagent, B, employed as one of the starting materials in reaction (a), the following reaction is completed wherein R is methyl.

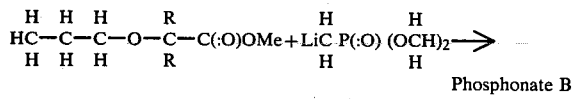

Phosphonate B

Contact of the lithium salt of dimethylmethylphosphonate with methyl propoxyisobutyrate in solution with ethereal solvents such as tetrahydrofuran or ether at temperatures of −78° to −60° and usually at the temperature of a dry ice/acetone bath for periods ranging from 30 minutes to 120 minutes will produce the phosphonate of formula B. It is purified from the above reaction mixture by neutralizing with an appropriate amount of an organic acid such as acetic acid, followed by the use of common techniques such as column chromatography or distillation.

After preparation of Phosphonate B, its salt is combined with the γ-lactone of formula A in a Wadsworth-Emmons fashion to prepare enone C; as illustrated in reaction (a). The method of that reaction is as follows. The sodium or lithium salt of Phosphonate B is prepared by contact with a base such as sodium hydride or n-butyl lithium in ethereal solvents such as tetrahydrofuran or dimethoxyethane at ambient temperature. Then the salt is contacted with the γ-lactone, formula A, at temperatures 0° to 30° for about 30 to 90 minutes to form enone C. The reaction mixture is neutralized with an organic acid and the product is isolated by the usual technique of column chromatography.

The second part of Scheme A, which is represented by step (b), consists of the following reactions: reduction of the enone fragment to an allyl alcohol fragment; transesterification of the p-biphenylcarboxy group; and the formation of a mild reagent labile ether at each of the hydroxyl positions. The reduction of the enone fragment will be accomplished by any reducing agent which attacks only the carbonyl of the enone fragment. It is usual to employ a trialkyborohydride such as lithium tri-sec-butylborohydride in a stoichiometric ratio to the enone and the reaction is conducted at about dry ice temperature for 30 to 90 minutes in ethereal solvents followed by neutralization. The product can then be isolated by the usual purification techniques.

This reduction of the enone produces two compounds which are the α and β forms of the allyl alcohol. They are diasteromers and are separable by common techniques. Although only the α form is shown, it is herein disclosed that the β form is equally functionable in the processes of the invention. Therefore, although Schemes A, B, C and D depict only the α form, it is implied that the β form is included.

Transesterification of the p-biphenyl ester is accomplished in basic alcoholic media. Any weak base which is sufficient to hydrolyze esters will accomplish the task and the usual reaction conditions are contact of the ester with potassium carbonate in methanol for about an hour, neutralization and isolation by the extraction.

Conversion of the hydroxyl functions at C-11 and C-15 to mild reagent labile ethers completes step (b) and produces the γ-lactone of formula D.

Any group which will function as a mild reagent labile protecting group can be employed as the moiety $R^1$. Some groups are tetrahydropyran-2-yl and dimethyl-t-butyl silyl. In the case wherein $R^1$ is tetrahydropyran-2-yl the method of formation usually employs an excess of 2,3-dihydropyran in methylene chloride with p-toluenesulfonic acid as a catalyst and reaction times of 30 to 90 minutes. In the case wherein $R^1$ is dimethyl-tert-butylsilyl, the method of formation usually employs an excess of dimethyl-tert-butylsilyl chloride and a base such as imidazole in dimethylformamide at temperatures of 25°–100° and reaction times of 3–24 hours. After following either of these procedures, the product γ-lactone of formula D is isolated by basic extraction and column chromatography.

Scheme A
ω-chain sequence

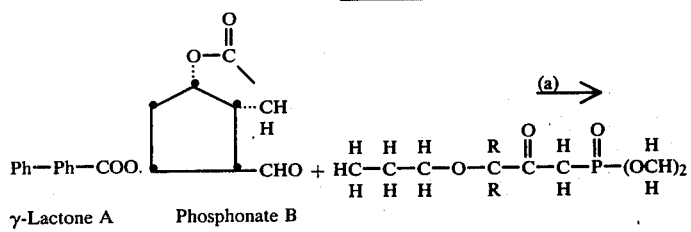

γ-Lactone A     Phosphonate B

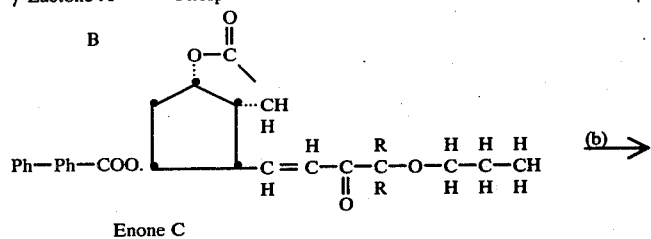

Enone C

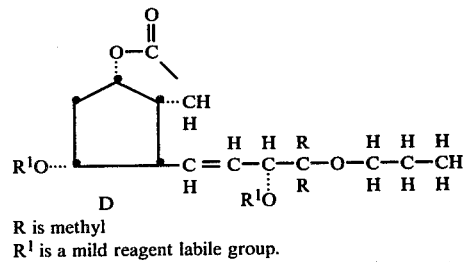

D

R is methyl
$R^1$ is a mild reagent labile group.

Scheme B
γ-chain sequence

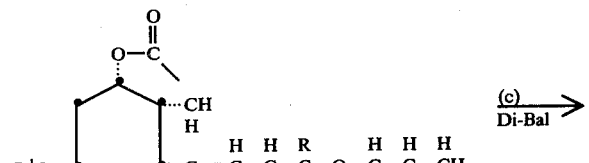

D

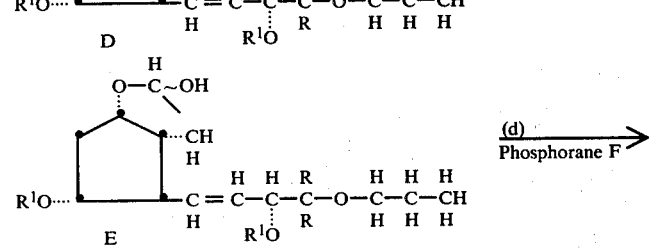

E

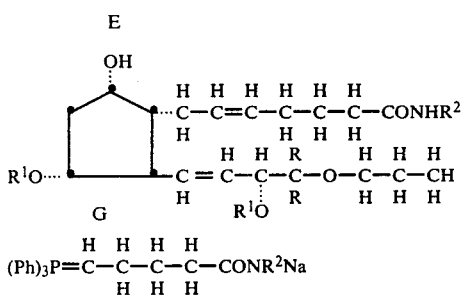
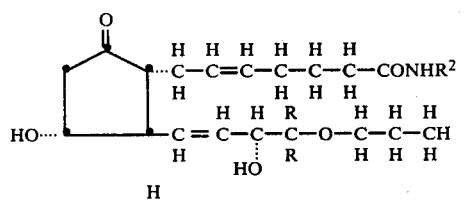
Phosphorane F
R and R$^1$ are defined supra.
R$^2$ is selected from alkylsulfonyl having from one to four carbon atoms, alkanoyl having two to five carbon atoms and benzoyl.
Scheme C
Products of the Invention
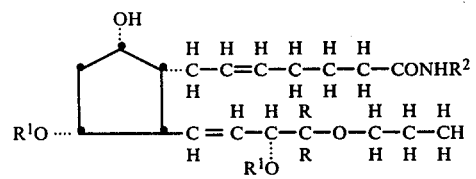
↑ oxidation
(e) R$^1$ cleavage
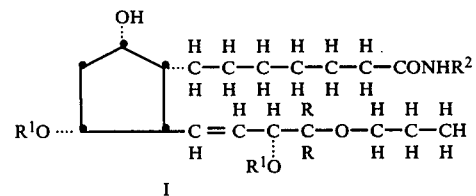
↓ (f) hydrogenation
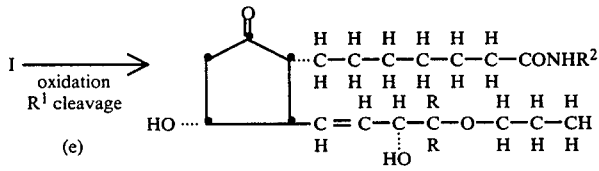
R, R$^1$ and R$^2$ are defined supra.
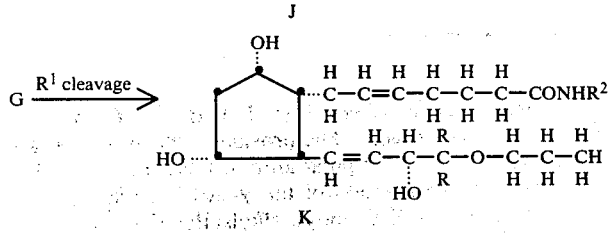

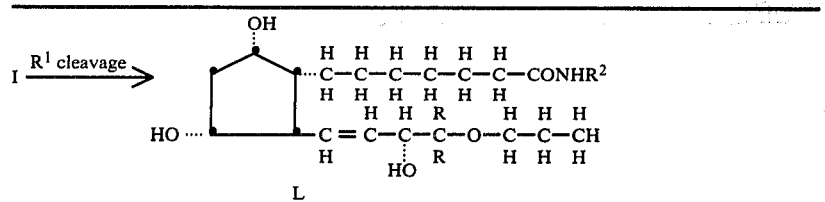

L

R, R¹ and R² are defined supra.

Scheme D

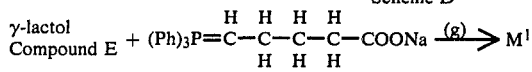

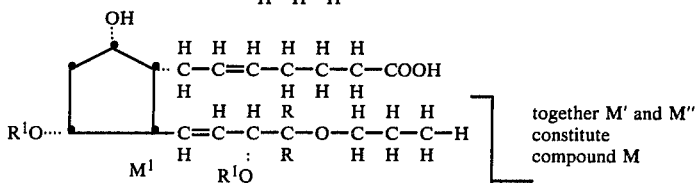

catalytic
hydrogenation
(f)

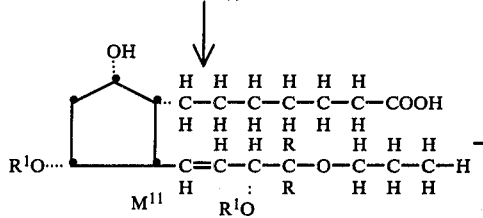

R and R¹ are defined supra.

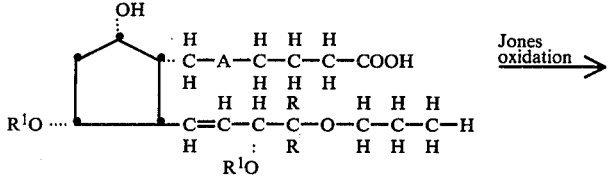

M

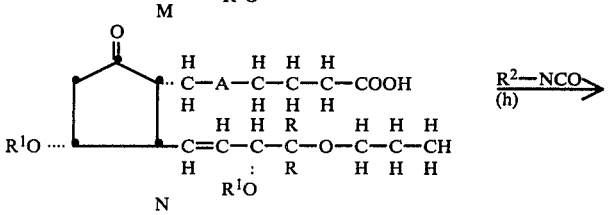

N

R¹ cleavage ↓ compound H (A = cis vinylene) or compound J (A = ethylene).
R, R¹ and R² are defined supra.

Scheme B is the α-chain synthesis which forms prostaglandins of formula G by combining the γ-lactol of formula E with elements of the Phosphorane of formula F. The requisite methods of this scheme follow those of Corey (op. cit.) and of U.S. Pat. No. 3,954,741. Briefly, the γ-lactone D is reduced to the γ-lactol E by diisobutylaluminumhydride (DiBal) at −78° C. to −60° C. in an inert solvent. The prostadienamide of formula G is then prepared in polar aprotic solvent at 10° to 50° C. by a Wittig reaction of the γ-lactol E with the sodium salt of [4-(N-alkanoyl, alkylsulfonyl or benzoyl)- aminocarbonyl)-n-butyl]triphenylphosphorane. Phosphorane F, the alkanoyl group being two to five carbon atoms in length and the alkylsulfonyl group being one to four carbon atoms in length. The Phosphorane F is prepared in situ from the corresponding phosphonium bromide or chloride and the sodium salt of dimethyl sulfoxide immediately before the Wittig reaction.

The reactions represented by Scheme C are those which convert prostadienamide G into some products of the present invention: prostadienamides of formulas H and K and the prostenamides of formulas J and L. In Scheme C, step (e) consists of two reactions, the first of which is a Jones oxidation of the C9-hydroxyl to a keto group and the second of which is the cleavage of the mild reagent labile protecting group $R^1$ producing a hydroxyl group. Step (f) of Scheme C is a catalytic hydrogenation of the C5-C6 double bond to a single bond. The methods of these steps are known to those familiar with the art.

Briefly, the Jones oxidation contacts prostadienamide G or prostenamide I with Jones reagent (chromic acid in sulfuric acid and water) in acetone solution for about 5 minutes at $-20°$ C. to $0°$ C. followed by quenching with isopropanol.

Cleavage of the mild reagent labile group, $R^1$, which produces compounds H, J, K and L, is accomplished by contacting the appropriate prostenamide or prostadienamide compound with a mixture of acetic acid and water for 5 to 24 hours at $20°$ to $40°$ C. or if desired in the silyl ether case, with the mild base tetra-alkylammonium fluoride having one to four carbons in each of the alkyl provided that the prostaglandin compound is other than a PGE.

Catalytic hydrogenation is accomplished by agitation of prostadienamide G in methanol, ethanol or ethyl acetate solution with a noble metal catalyst such as palladium on carbon under one atmosphere of hydrogen at $-20°$ C.

Alternatively, prostadienamide H and prostenamide J may be synthesized by the method illustrated by Scheme D. The first step (g) of Scheme D which prepares prostadienoic acid $M^1$ is the attachment of the α-chain to the γ-lactol of formula E. The attachment is achieved by a Wittig reaction of the γ-lactol E with the sodium salt of (4-carboxy-n-butyl)triphenylphosphorane in a polar aprotic solvent at $10°$ to $50°$ C. In accord with most steps of the reaction sequence this step follows the method of Corey (op. cit.) and that described in U.S. Pat. No. 3,958,284.

In the optional second step of Scheme D the prostadienoic acid $M^1$ may be hydrogenated using the same conditions described for step (f) of Scheme C to produce the prostenoic acid of formula $M^{11}$. Together the compounds $M^1$ and $M^{11}$ form prostaglandin intermediate M wherein A, which represents the C5 and C6 carbon atoms, can be cis-vinylene or ethylene.

In the third step of Scheme D the 9-hydroxy group of intermediate M is oxidized to a keto group using the Jones oxidation procedure described above and produces prostaglandin intermediate N.

In the fourth step (h) of Scheme D the prostaglandin acid N is converted into an N-alkylsulfonyl, N-alkanoyl or N-benzoyl carboxamide prostaglandin intermediate O by reaction with an acyl or sulfonyl isocyanate, the method of which follows wellknown art; [A. J. Speziale, et. al., *J. Org. Chem.*, 30, 4306 (1965), C. O. Hurd and A. G. Prapas, *J. Orig. Chem.*, 24, 388 (1959), reactions of isocyanates with carboxylic acids in "Survey of Organic Synthesis", C. A. Beuhler, D. E. Pearson, Wiley Interscience, New York, 1970, N-acylation of amides and imides, J. March, "Advanced Organic Chemistry: Reactions, Mechanisms and Structure", McGraw-Hill, New York, 1968, p.340]. The preferred method is that of Speziale and Hurd where an acyl or sulfonyl isocyanate is reacted with prostaglandin acid intermediate N in an inert solvent such as ether, tetrahydrofuran or methylene chloride using a weak base such as triethyl amine at temperatures ranging from ambient to reflux for 0.1 to 6 hours. The intermediate carboxamide O is then deprotected by cleaving the protecting group $R^1$ as described above and produces compound H wherein A is cis vinylene or compound J wherein A is ethylene.

In numerous in vivo and in vitro tests, it has been established that the prostaglandin compounds of the present invention exhibit extreme selectivity. Their biological achievement is the diminuation of many of the physiological activities of the natural prostaglandins while maintaining activity in one area. The tests which allow such determination of selectivity include among others, a test for effect on isolated smooth muscle from guinea pig and rat uterus, inhibition of stimulated gastric acid secretion in the dog, effect on dog blood pressure, inhibition of cold stress-induced ulceration in the rat and diarrheal effect in the mouse.

After comparison to the responses by natural prostaglandins, the physiological responses observed in these tests are useful in determining the utility of the test substance for the treatment of natural and pathological conditions. Based upon such comparison, the determined utility of the prostaglandin compounds of the present invention is antisecretion. This selective utility is made apparent by the existence of oral gastric antisecretory activity in the prostaglandin compounds of the present invention which is much greater than that of the natural prostaglandins and the diminuation of such determined activities as hypotensive activity, diarrheal activity, uterine stimulant activity and bronchodilator activity. Prime examples of the therapeutic importance with respect to selectivity are N-methanesulfonyl and N-acetyl 16,16-dimethyl-17-oxaprostaglandin $E_2$ carboxamide.

The new compounds of this invention can be used in a variety of pharmaceutical formulations which contain one of the prostaglandin compounds or alternatively, when the prostaglandin compound is an N-alkylsulfonylcarboxamide, the pharmaceutically acceptable salt. They may be administered in the same manner as natural prostaglandins by a variety of routes, such as intravenous and oral, among others, as anti-secretory agents for the control of and prophylaxis of peptic ulceration.

For pharmaceutical formulation and for solid compounding of the prostaglandin compounds of the present invention having an N-alkylsulfonylcarboxamide group, the useful pharmacological acceptable salts are those with pharmacologically acceptable metal cations, ammonium, amine cations, or quaternary ammonium cations.

Especially preferred metal cations are those derived from the alkali metal, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triethylamine, ethylamine, benzylamine, α-phenylethylamine, β-phenylethylamine, as well as heterocyclic amines, e.g., piperidine, morpholine, pyrrolidine, and piperazine as well as amines containing water-solubilizing or hydrophilic groups, e.g., mono-, di-, and triethanolamine, ethyldiethanolamine, galactamine, N-methylglucosamine, epherdrine, phenylephrine, epinephrine, procaine and the like.

Examples of suitable pharmacologically acceptable quaternary ammonium cations are tetramethylammonium, tetraethylammonium, benzyltrimethylammonium, phenyltriethylammonium and the like.

The new compounds of this invention can be used in a variety of pharmaceutical preparations which contain one of the prostaglandin compounds or a pharmaceutically acceptable salt thereof when the prostaglandin compound has an N-alkylsulfonylcarboxamide group. They may be administered by several routes as described above. Although the particular dose, formulation and route of administration are dependent upon each patient's unique condition and the wisdom of his attending physician, the guidelines set forth infra for the 16, 16-diethyl-17-oxaprostaglandin compounds described their usefulness as peptic antisecretory agents. For treatment of ulcers, these compounds may be orally administered in the form of capsules or tablets at doses of 0.1-5 mg. of prostaglandin compound per dose.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. The spectral data were obtained on a Varian T-60 or an A-60 NMR and a Perkin-Elmer Grating Infrared Spectrometer. The infrared data are given in microns and the NMR data are given in parts per million using TMS as a standard. Melting points are uncorrected and are in °Centigrade.

In general, the temperatures of the reactions described in the examples, when unspecified, will be taken to mean ambient or room temperature which varies from 15° to 30° C.

The time requirements of the reactions described in the examples, unless otherwise stated, were determined by monitoring with thin layer chromatography (TLC). The usual TLC system was silica-gel on glass (E. Merck-Silica Gel plates, E. Merck, Dormstadt, W. Germany) with benzene/ether or methanol/chloroform as eluants and vanillin/ethanol or iodine as developers. ["Introduction to Chromatography" J. M. Bobbitt, A. E. Schwarting, R. J. Gritter, Van Nostrand-Reinhold, N.Y. 1968]. As a general rule, the reaction in question was deemed essentially complete when the TLC spot representing the critical starting material had disappeared or had quit changing in appearance.

PREPARATION A

Dimethyl 2-Oxo-3,3-dimethyl-4-oxaheptylphosphonate (2)

A solution of 73.0 g. (568 mmoles) dimethyl methylphosphonate in 600 ml. dry tetrahydrofuran was cooled to −78° in a dry nitrogen atmosphere. To the stirred phosphonate solution was added 294 ml. of 2.0 M n-butyllithium in hexane solution dropwise over a period of 60 minutes at such a rate that the reaction temperature never rose above −65°. After an additional 10 minutes stirring at −78°, 51.3 g. (293 mmole) methyl propoxyisobutyrate as added dropwise at a rate that kept the reaction temperature less than −70° (20 minutes). After 0.5 hours at −78° the reaction mixture was allowed to warm to ambient temperature, neutralized with 35 ml. acetic acid and rotary evaporated to a white gel. The gelatinous material was taken up in 100 ml. water, the aqueous phase extracted with 150 ml. portions of methylene chloride (3x), and concentrated (water aspirator to a crude residue and distilled, b.p. 98°-100° (0.6 mm) to give 60.3g. (93%) dimethyl 2-oxo-3,3-dimethyl-4-oxa heptylphosphonate (2).

The nmr spectrum (CDCl$_3$) showed a doublet centered at 3.81δ(J=11.5 cps, 6H) a triplet centered at a 3.29δ(2H), a multiplet at 1.31-1.83δ(2H), a doublet centered at 3.34 (J=22 cps, 2H) a singlet at 1.30δ(6H) and a triplet at 0.93δ(3H).

EXAMPLE 1

2-[3α-p-Phenylbenzoyloxy-5α-hydroxy-2β-(3-oxo-4,4-dimethyl-5-oxatrans-1-octen-1-yl)-cyclopent-1α-yl]Acetic Acid, α-lactone (3)

Dimethyl 2-oxo-3,3-dimethyl-4-oxaheptylphosphonate (2) (3.48 g., 15.7 mmole) in 10 ml. anhydrous THF was added dropwise to 660 mg. (15.7 mmole) 57% sodium hydride in 220 ml. dry THF in a dry nitrogen atmosphere at room temperature. After 40 min. of stirring, 5.0 g. (14.3 mmole) 2-[3α-p-phenylbenzoyloxy-5α-hydroxy-2β-formylcyclopent-1αyl]acetic acid, α-lactone was added in one portion followed by 50 ml. anhydrous THF. After 60 minutes the reaction mixture was quenched with 1.5 ml. glacial acetic acid, evaporated, diluted with 200 ml. ethyl acetate and washed successively with 30 ml. saturated sodium bicarbonate solution (4 ×), 30 ml. water (2 ×), 30 ml. saturated brine (1 ×), dried (Na$_2$SO$_4$) and evaporated to yield 40 g. (59%) 2-[3α-p-phenylbenzoyloxy-5α-hydroxy-2β-(3-oxo-4,4-dimethyl-5-oxa-trans-1-octen-1-yl)cyclopent-1α-yl]acetic acid, γ-lactone (3) as a solid, m.p. 115°-116° (methylenechloride-hexane).

The IR spectrum (CHCl$_3$) of the product 3 exhibited absorption bands at 1775 cm$^{-1}$ (strong), and 1630 cm$^{-1}$ (medium). The nmr spectrum (CDCl$_3$) exhibited a multiplet at 7.23-8.18 δ(9H), a doublet centered at 6.85δ(2H), a multiplet from 4.9-5.68δ (2H), a triplet at 3.2 (2H), a multiplet from 1.3-1.8δ(2H) a singlet at 1.28δ(6H), a triplet at 0.87δ, and a multiplet from 2.2-3.0δ. C,H analysis, calculated for C$_{29}$H$_{32}$O$_6$:

| Cal'd | Found |
|---|---|
| C- 73.1 | 73.0 |
| H- 6.8 | 7.0 |

EXAMPLE 2

2-[3α-p-Phenylbenzoyloxy-5α-hydroxy-2β-(3β-hydroxy-4,4-dimethyl-5-oxa-trans-1-oceten-1-yl)cyclopent-1α-yl]acetic acid, δ-lactone (4) and 2-[3α-Phenylbenzoyloxy-5α-hydroxy-2β-(3α-hydroxy-4,4-dimethyl5-oxa-trans-1-octen-1-yl)cyclopent-1α-yl]acetic acid, γ-lactone (5)

To a solution of 17.2 g. (40.4 mmole) 2-[3α-p-phenylbenzoyloxy-5α-hydroxy-2β-(3-oxo-4,4-dimethyl-5-oxa-trans-1-octen-1-yl)-cyclopent-1α-yl]acetic acid, γ-lactone (3) in 200 ml. dry THF/ether (4:1) in a dry nitrogen atmosphere at −78° was added dropwise 104 ml. (43.0 mmole) of a 0.413 M lithium tri-sec-butylborohydride solution. After stirring at −78° and 0.5 hours the reaction was quenched with 91 ml. of acetic acid/water (40:60). The reaction mixture was allowed to warm to room temperature and then combined with 300 ml. water and 400 ml. methylene chloride. The methylene chloride layer was separated and the aqueous layer further extracted with methylene chloride (2 × 100 ml.). After washing the combined organic layers with brine (100 ml.), drying ($Na_2SO_4$) and concentrating (water aspirator), the resultant residue was purified by column chromatography on silica gel (Baker "Analyzed" Reagent 60–200 mesh) using benzene/ethyl acetate (7:1) as eluent. After elution of less polar impurities a fraction containing 9.0 g. 2-[3α-p-phenylbenzoyloxy-5α-hydroxy-2β-(3-oxo-4,4-dimethyl-5-oxaoctan-1-yl)-cyclopent-1αyl]acetic acid, γ-lactone (19), a fraction containing 3.7 g. 2-[3α-p-phenylbenzoyloxy-5α-hydroxy--(3α-hydroxy-4,4-dimethyl-5-oxa-trans-1-octen-1-yl)cyclopent1α-yl]acetic acid, γ-lactone (5), a 1.3 g. fraction of mixed 4 and 5 and finally a fraction (2.5 g.) of 2-[3α-p-phenylbenzoyloxy5α-hydroxy-2β-(3β-hydroxy-4,4-dimethyl-5-oxa-trans-1-octen-1-yl))cyclopent-1α-yl]acetic acid, γ-lactone (4).

The IR spectra ($CHCl_3$9 of 4 and 5 had strong absorptions at 1770 and 1715 $cm^{-1}$ and an absorption at 970 $cm^{-1}$.

EXAMPLE 3

2-[3α,5α-Dihydroxy-2β-(3α-hydroxy-4,4-dimethyl-5-oxa-trans-1-octen-1-yl)cyclopent-1α-yl]acetic acid, γ-lactone (6)

A heterogeneous mixture of 3.7 g. (7.8 mmole) of 2-[3α-p-phenylbenzoyloxy-5α-hydroxy-2β-(3α-hydroxy-4,4-dimethyl-5-oxa-trans-1-oceten-1-yl)cyclopent-1α-yl]acetic acid, γ-lactone (5), 50 ml. of absolute methanol and 1070 mg. of finely powdered, anhydrous potassium carbonate was stirred at room temperature for one hour, then cooled to 0°. To the cooled solution was added 15.6 ml. (15.6 mmole) of 1.0N aqueous hydrochloric acid. After stirring at 0° for an additional 10 minutes, 50 ml. of water was added with concomitant formation of methyl p-phenylbenzoate which was collected by filtration. The filtrate was saturated with solid sodium chloride, extracted with ethyl acetate (3×150 ml.), the combined organic extracts were washed with saturated sodium bicarbonate (50 ml.), brine (50 ml.) and dried ($MgSO_4$) and concentrated to give 2.0 g. (87%) of viscous oily 2-[3α,5α-dihydroxy-2β-(3α-hydroxy-4,4-dimethyl-5-oxa-trans-1-octen-1-yl)cyclopent-1α-yl]acetic acid, γ-lactone (6).

The IR spectrum ($CHCl_3$) exhibited a strong absorption at 1770 $cm^{-1}$ and medium absorption at 965 $cm^{-1}$.

EXAMPLE 4

2-[3α,5α-Dihydroxy-2β-(3β-hydroxy-4,4-dimethyl-5-oxa-trans-1-octen-1-yl)cyclopent-1α-yl]acetic acid, γ-lactone (6a)

A heterogeneous mixture of 2.5 g. (5.25 mmole) of 2[3α-p-phenylbenzoyloxy-5α-hydroxy-2β-(3β-hydroxy-4,4-dimethyl-5-oxa-trans-1-octen-yl)cyclopent-1α-yl]acetic acid, γ-lactone (4), 40 ml. of absolute methanol and 720 mg. of finely powdered, anhydrous potassium carbonate was stirred at room temperature for one hour, then cooled to 0°. To the cooled solution was added 10.4 ml. (10.4 mmole) of 1.0N aqueous hydrochloric acid. After stirring at 0° for an additional 10 minutes, 40 ml. of water was added with concomitant formation of methyl p-phenylbenzoate which was collected by filtration. The filtrate was saturated with solid sodium chloride, extracted with ethyl acetate (3×100 ml.), the combined organic extracts were washed with saturated sodium bicarbonate (40 ml.), brine (40 ml.) and dried ($MgSO_4$) and concentrated to give 1.0 g. (64%) of viscous, oily 2-[3α,5α-dihydroxy-2β-(3β-hydroxy-4,4-dimethyl-5-oxa-trans-1-octen-1-yl)cyclopent-1α-yl]acetic acid, γ-lactone (6a).

The IR spectrum ($CHCl_3$) exhibited a strong absorption at 1770 $cm^{-1}$ and medium absorption at 965 $cm^{-1}$.

EXAMPLE 5

2-[5α-Hydrocy-3α-(tetrahydropyran-2-yloxy)-2β-(3α-[tetrahydropyran-2-yloxy]-4,4-dimethyl-5-oxa-trans-1-octen-1-yl)cyclopent-1α-yl]acetic acid, γ-lactone (7)

To a solution of 2.0 g. (6.7 mmole) 2-[3α,5α-dihydroxy-2β-(3α-hydroxy-4,4-dimethyl-5-oxa-trans-1-octen-yl)cyclopent-1α-yl]-acetic acid, γ-lactone (6) in 40 ml. anhydrous methylene chloride and 2 ml. of 2,3-dihydropyran at 0° in a dry nitrogen atmosphere was added 27 mg. p-toluenesulfonic acid, monohydrate. After stirring for 30 minutes, the reaction mixture was combined with 100 ml. ether, the ether solution washed with saturated sodium bicarbonate (2×30 ml.) and then saturated brine (1×30 ml.), dried ($Na_2S0_4$) and concentrated to yield 2.5 g. of 2-[5α-hydroxy-3α-(tetrahydropyran-2-yloxy)-2β-(3α-[tetrahydropyran-2-yloxy]-4,4-dimethyl-5-oxa-trans-1-octen-1-yl)cyclopent-1α-yl]acetic acid, γ-lactone (7) after column chromatography.

The IR ($CHCl_3$) spectrum had a medium absorption at 970 $cm^{-1}$.

EXAMPLE 6

2-[5α-Hydroxy-3α-(tetrahydropyran-2-yloxy)-2β-(3β-[tetrahydropyran2-yloxy]-4,4-dimethyl-5-oxa-trans-1-octen-1-yl)cyclopent-1α-yl]-acetic acid, γ-lactone (7a):

To a solution of 1.0 g. (3.36 mmole) 2-[3γ,5γ-dihydroxy-2β(3β-hydroxy-4,4-dimethyl-5-oxa-trans-1-octen-1-oceten-1-yl)cyclopent-1α-yl]acetic acid, γ-lactone (6a) in 30 ml. anhydrous methylene chloride and 1.0 ml. of 2,3-dihydropyran at 0° in a dry nitrogen atmosphere was added 15 mg. p-toluenesulfonic acid, monohydrate. After stirring for 30 minutes, the reaction mixture was combined with 100 ml. ether, the ether solution washed with saturated sodium bicarbonate (1×15 ml.) then saturated brine (1×15 ml.), dried ($MgSO_4$) and concentrated to yield 912 mg. of2-[5α-hydroxy3α-

(tetrahydropyran-2-yloxy)-2β-(3β-[tetrahydropyran-2-yloxy]4,4-dimethyl-5-oxa-trans-1-octen-1-yl)cyclopent-1α-yl]acetic acid, γ-lactone (7a) after column chromatography.

The IR (CHCl$_3$) spectrum had a medium absorption at 970 cm$^{-1}$.

EXAMPLE 7

2-[5α-Hydroxy-3α-(tetrahydropyran-2-yloxy)-2β-(3α-[tetrahydropyran-2-yloxy]-4,4-dimethyl-5-oxa-trans-1-octen-1-yl)cyclopent1α-yl]acetaldehyde, γ-hemiacetal (8)

A solution of 1.05 g. (2.2 mmole) of 2-[5α-hydroxy-3α-(tetrahydropyran-2-yloxy)-2β-[3α-[tetrahydropyran-2-yloxy]-4,4dimethyl-5-oxa-trans-1-octen-1-yl)cyclopent-1α-yl]acetic acid, γ-lactone (7) in 20 ml. dry toluene was cooled to −78° in a dry nitrogen atmosphere. To this cooled solution was added 3.0 ml. of 20% diisobutylaluminum hydride in n-hexane (Alfa Inorganics) dropwise at such a rate so that the internal temperature never rose above −65° (5 minutes). After an additional 30 minutes of stirring at −78°, 105 mg. of acetic acid was added and the reaction mixture was allowed to warm to room temperature. The reaction mixture was combined with 100 ml. ether, washed with 50% sodium potassium tartrate solution (20 ml.), dried (Na$_2$SO$_4$) and concentrated to yield 880 mg. (2-[5α-hydroxy-3α-(tetrahydropyran2-yloxy)-2β-(3α-[tetrahydropyran-2-yloxy]-4,4-dimethyl-5-oxa-trans-1-octen-1-yl)cyclopent-1-yl]acetaldehyde, γ-hemiacetal (8) after column chromatography. The IR spectrum exhibited a medium absorption at 970 cm$^{-1}$.

EXAMPLE 8

2-[5α-Hydroxy-3α-(tetrahydropyran-2-yloxy)-2β-(3β-[tetrahydropyran-2-yloxy]-4,4-dimethyl-5-oxa-trans-1-octen-1-yl)cyclopent1α-yl]acetaldehyde,γ-hemiacetal (8a):

A solution of 920 mg. (1.92 mmole) 2-[5α-hydroxy-3α-(tetrahydropyran-2-yloxy)-2β-(3β-[tetrahydropyran-2-yloxy-4,4-dimethyl5-oxa-1-trans-1-octen-1-yl)cyclopent-1α-yl] acetic acid, γ-lactone (7a) in 20 ml. dry toluene was cooled to −78° in a dry nitrogen atmosphere. To this cooled solution was added 2.58 ml. of 20% diisobutylaluminum hydride in n-hexane (Alfa Inorganics) dropwise at such a rate so that the internal temperature never rose −65° (15 minutes). After an additional 45 minutes of stirring at −78° , anhydrous acetic acid (80 mg.) was added and the reaction mixture was allowed to warm to room temperature. The reaction mixture was combined with 100 ml. ether, washed with 50% sodium potassium tartrate solution (20 ml.), dried (Na$_2$SO$_4$) and concentrated to yield 645 mg. 2-[5α-hydroxy-3α-(tetrahydropyran-2-yloxy)-2β-(3β-[tetrahydropyran-2-yloxy]-4,4-dimethyl-5-oxa-trans-1-octen-1-yl)cyclopent-1α-yl]acetaldehyde, γ-hemiacetal (8a) after column chromatography. The IR spectrum exhibited a medium absorption at 970 cm$^{-1}$.

EXAMPLE 9

9α-Hydroxy-11α,15α-bis-(tetrahydropyran-2-yloxy)-16,16-dimethyl-17-oxa-cis-5-trans-13-prostadienoic acid (9):

To a solution of 4.04 g. (9.1 mmole) (4-carbohydroxy-n-butyl) triphenylphosphonium bromide in a dry nitrogen atmosphere in 2.0 ml. dry dimethyl sulfoxide was added 9.3 ml. (16.7 mmole) of a 1.8M solution of sodium methylsufinylmethide in dimethyl sulfoxide. To this red ylide solution was added dropwise a solution of 1453 mg. (3.04 mmole) 2-[5α-hydroxy-3α-(tetrahydropyran-2-yloxy)-2β-(3α-[tetrahydropyran-2-yloxy]-4,4-dimethyl-5-oxa-trans-1-octen-1-yl)cyclopent-1α-yl]acetaldehyde, γ-hemiacetal (8) in 15.0 ml. dry dimethyl sulfoxide over a period of 20 minutes. After an additional 45 min. stirring at room temperature, the reaction mixture was poured onto ice water and 17 ml. 1N HCl. The acidic solution was extracted with ethyl acetate (3×200 ml.) and the combined organic extracts washed with water (2×50 ml.), brine (50 ml.), dried (MgSO$_4$) and evaporated to a residue. The residue was purified by column chromatography on silica gel (Baker "Analyzed" Reagent 60–200 mesh) using chloroform and ethyl acetate as eluents. After removal of high R$_f$impurities, 1013 mg. of 9α-hydroxy- 11α,15α-bis-(tetrahydropyran-2-yloxy)-16,16-dimethyl-17-oxa-cis-5-trans-13-prostadienoic acid was collected.

EXAMPLE 10

9α-Hydroxy-11α,15β-bis-(tetrahydropyran-2-yloxy)-16,16-dimethyl-17-oxa-cis-5-trans-13-prostadienoic acid (9a)

To a solution of 1770 mg. (4.0 mmole) (4-carbohydroxy-n-butyl)-triphenylphosphonium bromide in a dry nitrogen atmosphere in 10 ml. dry dimethyl sulfoxide was aded 4.1 ml. (7.35 mmole) of a 1.8M solution of sodium methylsufinylmethide in dimethyl sulfoxide. To this red ylide solution was added dropwise a solution of 645 mg. (1.34 mmole) 2-[5α-hydroxy-3α-(tetrahydropyran-2-yloxy)-2β-(3β-[tetrahydropyran-2-yloxy]-4,4-dimethyl-5-oxa-trans-1-octen-1-yl)-cyclopent-1α-yl]acetaldehyde, γ-hemiacetal (8a) in 10 ml. dry dimethyl sulfoxide over a period of 20 minutes. After an additional 2 hours stirring at room temperature, the reaction mixture was poured onto ice water and 8 ml. 1N HCl. The acidic solution was extracted with ethyl acetate (3×150 ml.) and the combined organic extracts washed once with water (2×30 ml.), brine (30 ml.), dried (MgSO$_4$) and evaporated to a residue. The residue was purified by column chromatography on silica gel (Baker "Analyzed" Reagent 60–200 mesh) using chloroform and ethyl acetate as eluents. After removal of high R$_f$impurities, 694 mg. of 9α-hydroxy-11α,15β-bis-(tetrahydropyran-2-yloxy)-16,16-dimethyl-17-oxa-cis-5-trans-13-prostadienoic acid was collected.

EXAMPLE 11

9α-Hydroxy-11α,15α-bis-(tetrahydropyran-2-yloxy)-16,16-dimethyl-17-oxa-trans-13-prostenoic acid (10)

A solution, cooled to −20° C., of 1.0 mmole of 9α-hydroxy-11α,15α-bis-(tetrahydropyran-2-yloxy)-16,16-dimethyl-17-oxa-cis-5-trans-13-prostadienoic acid (9) in 50 ml. methanol is hydrogenated on an atmospheric hydrogenation apparatus using 1 g. of 10% palladium-on-carbon as a catalyst and a hydrogen atmosphere. After one equivalent of hydrogen is taken up, the catalyst can be filtered from the reaction mixture and the solvent can be removed in vacuo from the resultant filtrate. The residue can then be purified by the common techniques such as column or liquid high pressure chromatography to yield the title compound.

Using the same procedure, the prostadienoic acid (9a) of Example 10 can be converted into the corresponding prostenoic acid.

EXAMPLE 12

9-Oxo-11α,15α-bis-(tetrahydropyran-2-yloxy)-16,16-dimethyl-17-oxa-cis-5-trans-13-prostadienoic acid (11)

To a solution cooled to −10° under nitrogen of 526 mg. (0.06 mmole) 9α-hydroxy-11α,15α-bis-(tetrahydropyran-2-yloxy)-16,16-dimethyl-17-oxa-cis-5-trans-13-prostadienoic acid (9) in 30 ml. reagent grade acetone was added dropwise 0.47 ml. of Jones' reagent. After 20 minutes at −10°, 0.5 ml. 2-propanol was added and the reaction mixture was allowed to stir an additional 5 minutes at which time it was combined with 100 ml. ethyl acetate, washed with water (2×25 ml.), dried (MgSO$_4$) and concentrated to give 443 mg. iof 9-oxo-11α,15α-bis-(tetrahydropyran-2-yloxy)-16,16-dimethyl-17-oxa-cis-5-trans-13-prostadienoic acid (10).

Using the same procedure, the prostenoic acid compounds of Example 11 can be oxidizied to the corresponding PGE$_1$ and 15-epi-PGE$_1$ compounds, i.e. 9-oxo-11α,15αand 15β-bis-(THPO)-16,16-dimethyl-17-oxa-trans-13prostenoic acids.

EXAMPLE 13

9-Oxo-11α,15β-bis-(tetrahydropyran-2-yloxy)-16,16-dimethyl-17-ox-cis-5-trans-13-prostadienoic acid (11a)

To a solution cooled to −10° under nitrogen of 490 mg. (0.80 mmole) 9α-hydroxy-11α,15α-bis-(tetrahydropyran-2-yloxy)-16,16-dimethyl-17-oxa-cis-5-trans-13-prostadienoic acid (9a) in 25 ml. reagent grade acetone was added dropwise 0.43 ml. of Jones' reagent. After 20 minutes at −10° 0.5 ml. 2-propanol was added and the reaction mixture was allowed to stir an additional 5 minutes at which time it was combined with 75 ml. ethyl acetate, washed with water (3×10 ml.), dried (MgSO$_4$) and concentrated to give 440 mg. of 9-oxo-11α,15β-bis-(tetrahydropyran-2-yloxy)-16,16-dimethyl-17-oxa-cis-5-trans-13-prostadienoic acid (11a).

EXAMPLE 14

N-Acetyl 9-oxo-11α,15α-bis-(tetrahydropyran-2-yloxy)-5-cis-13-trans-16,16-dimethyl-17-oxa-prostadienamide (12)

To a solution of 726 mg. (1.32 mmole) of 9-oxo-11α,1-5α-bis-(tetrahydropyran-2-yloxy)-5-cis-13-trans-16,16-dimethyl-17-oxa-prostadienoic acid (11) and 133 mg. (1.32 mmole) of triethylamine in 25 ml. of methylene chloride was added 13 ml. of a ca. 0.6 M solution of acetyl isocyanate in ether. The mixture was stirred for 5 minutes then was neutralized with acetic acid, washed with water (3×40 ml.) and saturated brine (25 ml.), was dried with anhydrous magnesium sulfate and concentrated to provide the oily N-acetyl 9-oxo-11α,15α-bis-(tetrahydropyran-2-yloxy)-5-cis-13-trans-16,16-dimethyl-17-oxa-prostadienamide (12) weighing 857 mg.

Example 15

N-Acetyl 9-oxo-11α,15α-dihydroxy-5-cis-13-trans-16,16-dimethyl-17-oxa-prostadienamide (13):

A solution of 857 mg. N-acetyl 9-oxo-11α,15α-bis-(tetrahydropyran-2-yloxy)-5-cis-13-trans-16,16-dimethyl-17-oxa-prostadienamide (12) in 25 ml. of a 65:35 mixture of glacial acetic acid:water was stirred under nitrogen at 25° for 20 hours then was concentrated by roatary evaporation. The resultant crude oil was purified by column chromatography on silica gel (Mallinckrodt CC-7 100–200 mesh) using mixtures of chloroform:ethyl acetate as eluents. After elution of less polar impurities, the oily N-acetyl 9-oxo-11α,15α-dihydroxy-5-cis-13-trans-16,16-dimethyl-17-oxa- prostadienamide (13) weighing 102 mg. was collected.

In addition the other N-alkanoyl, N-alkylsulfonyl or N-benzoyl PGE$_2$ and PGE$_1$ carboxamides of the present invention may be synthesized according to the methods of Examples 14 and 15 by substituting the appropriate alkylsulfonyl, alkanoyl or benzoyl isocyanate for acetyl isocyanate in Example 14 and if appropriate, by substituting 9-oxo-11α,15α-bis-(THPO)-16,16-dimethyl-17-oxa-trans-13-prostenoic acid from Example 12 for prostadienoic acid (11) in Example 14.

EXAMPLE 16

N-Methanesulfonyl 9α-hydroxy-11α,15α-bis-(tetrahydropyran-2-yloxy)-16,16-dimethyl-17-oxa-5-cis-13-trans-prostadienamide (14)

To a solution of 2.76 g. (5.3 mmole) [4-(methanesulfonylaminocarbonyl)-n-butyl]triphenylphosphonium bromide in a dry nitrogen atmosphere in 5.0 ml. dry dimethyl sulfoxide was added 4.5 ml. (10.1 mmole) of a 2.24M solution of sodium methylsulfinylmethide in dimethylsulfoxide. To this red ylide solution was added dropwise a solution of 829 mg. (1.77 mmole) 2-[5α-hydroxy-3α-(tetrahydropyran-2-yloxy)-2β-(3β-[tetrahydropyran-2-yloxy]-4,4-dimethyl-5-oxa-trans-1-octen-1-yl)cyclopent-1α-yl]-acetaldehyde, γ-hemiacetal (8) in 2.0 ml. dry dimethyl sulfoxide over a period of 20 minutes. After an additional 45 minutes stirring at room temperature, the reaction mixture was poured onto ice water. The basic aqueous solution was acidified to pH~3 with 1 N. aqueous hydrochloric acid. The acidic solution was extracted with ethyl acetate (3×20 ml.) and the combined organic extracts washed once with water (10 ml.), dried (MgSO$_4$) and evaporated to a solid residue. This solid residue was triturated with ether and filtered. The filtrate was purified by column chromatography on silica gel (Baker "Analyzed" Reagent 60–200 mesh) using mixtures of chloroform:ethyl acetate as eluents. After removal of high R$_f$ impurities, the desired N-methanesulfonyl 9α-hydroxy-11α,15α-bis-(tetrahydropyran-2-yloxy)-16,16-dimethyl-17-oxa-5-cis-13-trans-prostadienamide (14) was collected as a colorless oil weighing 405 mg.

In addition the other N-alkylsufonyl, N-alkanoyl and N-benzoyl-9α-hydroxy-11α,15α-(bis-THPO)-16,16-dimethyl-17oxa-5-cis-13trans-prostadienamide intermediates of the present invention can be synthesized by the method of Example 16 by substituting the appropriate N-alkylsulfonyl, N-alkanoyl or N-benzoyl (-4-aminocarbonyl-n-butyl) triphenyl phosphonium salt for [4-(methanesulfonylaminocarbonyl)-n-butyl]triphenylphosphonium bromide in Example 16.

EXAMPLE 17

N-Methanesulfonyl 9α-Hydroxy-11α,15α-bis-(tetrahydropyran-2-yloxy-16,16-dimethyl-17-oxa-trans-13-prostenamide (18)

A solution, cooled to −20° C., of 1.0 mmole of N-Methanesulfonyl 9α-hydroxy-11α,15α-bis-(tetrahydropyran-2-yloxy)-16,16-dimethyl-17-oxa-trans-13-prostadienamide (14) in 50 ml. methanol is hydrogenated on an atmospheric hydrogenation apparatus using 1 g. of 10% palladium-on-carbon as a catalyst and a hydrogen atmosphere. After one equivalent of hydrogen is taken up, the catalyst can be filtered from the reaction mixture and the solvent can be removed in vacuo from the resultant filtrate. The residue can then be purified by the common techniques such as column or liquid high pressure chromatography to yield the title compound.

In addition the other N-alkylsulfonyl, N-alkanoyl and N-benzoyl 9α-hydroxy-11,15-bis-(THPO)-trans-13-prostenamide intermediates of the present invention may be synthesized by the method of Example 17 by substituting the appropriate prostadienamide from Example 16 for prostadienamide (14) in Example 17.

EXAMPLE 18

N-Methanesulfonyl 9α,11α,15α-trihydroxy-16,16-dimethyl-17-oxa-5-cis-13-trans-prostadienamide (15)

A solution of 400 mg. N-methanesulfonyl 9α-hydroxy-11α,15α-bis-(tetrahydropyran-2-yloxy)-16,16-dimethyl-17-oxa-5-cis-13, trans-prostadienamide (14) in 10.0 ml. of a 65:35 mixture of glacial acetic acid:water is stirred under nitrogen at 25° for 18 hours then is concentrated by rotary evaporation. The resultant crude product is purified by column chromatography on silica gel (Mallinckrodt CC-7 100-200 mesh) using mixtures of chloroform:ethyl acetate as eluent. After elution of less polar impurities the N-methanesulfonyl 9α,11α,15α-trihydroxy-16,16-dimethyl-17-oxa-5-cis-13-trans-prostadienamide (15) is collected.

In addition the other N-alkylsulfonyl, N-alkanoyl or N-benzoyl PGF$_{2\alpha}$ and PGF$_{1\alpha}$ carboxamides of the present invention may be synthesized according to the methods of Example 18 by substituting the appropriate 11,15-(bis-THP) PGF$_{2\alpha}$ intermediate from Example 16 for prostadienamide (14) in Example 18 or by substituting the appropriate 11,15-bis-(THP) PGF$_{1\alpha}$ intermediate from Example 17 for prostadienamide (14) in Example 18.

EXAMPLE 19

N-Methanesulfonyl 9-oxo-11α,15α-bis-(tetrahydropyran-2-yloxy)-16,16-dimethyl-17-oxa-5-cis-13-trans-prostadienamide (16)

To a solution cooled to −15° under nitrogen, of 400 mg. (0.645 mmole) N-methanesulfonyl 9α-hydroxy-11α,15α-bis-(tetrahydropyran-2-yloxy)-16,16-dimethyl-17-oxa-5-cis-13-trans-prostadienamide (14) in 10 ml. reagent grade acetone was added dropwise to 0.24 ml. of Jones' reagent. After 10 minutes at −10° 0.24 ml. 2-propanol was added and the reaction mixture was allowed to stir an additional 5 minutes at which time it was combined with 75 ml. ethyl acetate, washed with water (3×10 ml.), dried (MgSO$_4$) and concentrated to give 385 mg. of the colorless, oily N-methanesulfonyl 9-oxo-11α,15α-bis-(tetrahydropyran-2-yloxy)-16,16-dimethyl-17-oxa-5-cis-13-trans-prostadienamide (16).

EXAMPLE 20

N-Methanesulfonyl 9-oxo-11α,15α-dihydroxy-16,16-dimethyl-17-oxa-5-cis-13-trans-prostadienamide (17)

A solution of 385 mg. N-methanesulfonyl 9-oxo-11α,15α-bis-(tetrahydropyran-2-yloxy)-16,16-dimethyl-17-oxa-5-cis-13-trans-prostadienamide (16) in 20 ml. of a 65:35 mixture of glacial acetic acid:water was stirred under nitrogen at 25° for 20 hours then was concentrated by rotary evaporation. The resultant crude oil was purified by column chromatography on silica gel (Mallinckrodt CC-7 100-200 mesh) using mixtures of chloroform:ethyl acetate as eluents. After elution of less polar inpurities the oily N-methanesulfonyl 9-oxo-11α,15α-dihydroxy-16,16-dimethyl-17-oxa-5-cis-13-trans-prostadienamide (17) weighing 134 mg. was collected.

In addition the other N-alkylsulfonyl, N-alkanoyl and N-benzoyl PGE$_2$ and PGE$_1$ carboxamides of the present invention may be synthesized according to the methods of Examples 19 and 20 by substituting the appropriate 11,15-(bis-THP) PGE$_{2\alpha}$ intermediate from Example 16 for prostadienamide (14) in Example 19 or by substituting the appropriate 11,15-bis(THP) PGF$_{1\alpha}$ intermediate from Example 17 for prostadienamide (14) in Example 19.

What is claimed is:

1. A compound having the structure:

[structural formula]

wherein:
R$^2$ is selected from the group consisting of alkylsulfonyl having one to four carbon atoms, alkanoyl having two to five carbon atoms and benzoyl;
A is ethylene or cis-vinylene;
Z is alpha-hydroxy or beta-hydroxy;
each R is methyl;
and the pharmacologically acceptable salts thereof when R$^2$ is alkylsulfonyl.

2. A compound of claim 1 wherein R$^2$ is methanesulfonyl.

3. A compound of claim 1 wherein R$^2$ is acetyl.

4. A compound of claim 1 wherein R$^2$ is benzoyl.

5. N-(Methanesulfonyl)-9-oxo-11α,15α-dihydroxy-16,16-dimethyl-17-oxa-cis-5-trans-13-prostadienamide according to claim 2.

6. N-(Methanesulfonyl)-9-oxo-11α,15α-dihydroxy-16,16-dimethyl-17-oxa-trans-13-prostenamide according to claim 2.

7. N-(Acetyl)-9-oxo-11α,15α-dihydroxy-16,16-dimethyl-17-oxa-cis-5-trans-13-prostadienamide according to claim 3.

8. N-(Acetyl)-9-oxo-11α,15α-dihydroxy-16,16-dimethyl-17-oxa-trans-13-prostenamide according to claim 3.

9. A method to combat peptic ulceration which comprises administering orally or intravenously to a patient in need of such treatment an antisecretory effective amount of a prostaglandin of claim 1.

10. An antisecretory composition comprising a prostaglandin of claim 1 and an antisecretory effective amount of pharmaceutically acceptable carrier.